(12) United States Patent
Gingrich et al.

(10) Patent No.: US 12,257,221 B2
(45) Date of Patent: Mar. 25, 2025

(54) LEUCINE-ENRICHED KETOGENIC FORMULATIONS

(71) Applicant: AJINOMOTO CO., INC., Tokyo (JP)

(72) Inventors: Susan Gingrich, Ayer, MA (US); Robert Reed, Itasca, IL (US); Kenji Nagao, Tokyo (JP); Natsumi Nishikata, Tokyo (JP)

(73) Assignee: AJINOMOTO CO., INC., Tokyo (JP)

( * ) Notice: Subject to any disclaimer, the term of this patent is extended or adjusted under 35 U.S.C. 154(b) by 916 days.

(21) Appl. No.: 17/301,076

(22) Filed: Mar. 24, 2021

(65) Prior Publication Data

US 2021/0205252 A1     Jul. 8, 2021

Related U.S. Application Data

(63) Continuation of application No. PCT/IB2019/001126, filed on Oct. 2, 2019.

(60) Provisional application No. 62/741,506, filed on Oct. 4, 2018.

(51) Int. Cl.
| | |
|---|---|
| *A61K 31/198* | (2006.01) |
| *A23L 33/00* | (2016.01) |
| *A23L 33/115* | (2016.01) |
| *A23L 33/155* | (2016.01) |
| *A23L 33/19* | (2016.01) |
| *A23L 33/29* | (2016.01) |
| *A61K 8/44* | (2006.01) |

(Continued)

(52) U.S. Cl.
CPC .......... *A61K 31/198* (2013.01); *A23L 33/115* (2016.08); *A23L 33/155* (2016.08); *A23L 33/19* (2016.08); *A23L 33/29* (2016.08); *A23L 33/30* (2016.08); *A23L 33/40* (2016.08); *A61K 8/44* (2013.01); *A61K 9/0053* (2013.01); *A61P 25/08* (2018.01); *A61K 2800/92* (2013.01)

(58) Field of Classification Search
CPC ...... A61K 31/198; A61K 8/44; A61K 9/0053; A61K 2800/92; A61K 31/405; A61K 31/4172; A23L 33/115; A23L 33/155; A23L 33/19; A23L 33/29; A23L 33/30; A23L 33/40; A23L 33/12; A23L 33/17; A61P 25/08; A61P 25/28
See application file for complete search history.

(56) References Cited

FOREIGN PATENT DOCUMENTS

| | | |
|---|---|---|
| DE | 27 59 133 A1 | 7/1978 |
| EP | 3 501 516 A1 | 6/2019 |
| WO | WO-2012113415 A1 * | 8/2012 ............. A23L 1/296 |

(Continued)

OTHER PUBLICATIONS

Alessandro Pinto et al, "Anti-Oxidant and Anti-Inflammatory Activity of Ketogenic Diet: New Perspectives for Neuroprotection in Alzheimer's Disease", Antioxidants, vol. 7, No. 5, Apr. 28, 2018 (Apr. 28, 2018), p. 63, XP055648473.

(Continued)

*Primary Examiner* — Deborah D Carr
(74) *Attorney, Agent, or Firm* — Lippes Mathias LLP

(57) ABSTRACT

Described herein are nutritional compositions, such as ketogenic compositions, leucine-enriched amino acid mixtures, etc., useful, for example, for dietary management of intractable epilepsy. In some embodiments, the disclosure relates to methods of inhibiting epileptic seizures in a subject comprising administering to the subject a leucine-enriched amino acid mixture.

30 Claims, 3 Drawing Sheets

(51) Int. Cl.
    *A61K 9/00*         (2006.01)
    *A61P 25/08*       (2006.01)

(56) References Cited

FOREIGN PATENT DOCUMENTS

| WO | WO-2014008692 A1 * | 1/2014 | ........... A23C 9/1526 |
|---|---|---|---|
| WO | 2016/154575 A1 | 9/2016 | |
| WO | 2018/034330 A1 | 2/2018 | |

OTHER PUBLICATIONS

St-Pierre et al. "Butyrate is more ketogenic than leucine or octanoate-monoacylglycerol in healthy adult humans" Journal of Functional Foods—Journal of Functional Foods 32 (2017) 170-175, May 2017; DOI: 10.1016/j.i ff.2017.02.024.

Yudkoff et al. "The Ketogenic Diet and Brain Metabolism of Amino Acids: Relationship to the Anticonvulsant Effect" Annual Review of Nutrition 2007. 27:415-30, Apr. 19, 2007; DOI: 10.1146/annurev.nutr.27.061406.093722.

Hiroyuki Kato, "Leucine-enriched essential amino acids attenuate muscle soreness and improve muscle protein synthesis after eccentric contracations in rats", dated Mar. 14, 2015; 9 pages.

Examination Report No. 1 for AU 2019352571, dated Aug. 15, 2024.

Office Action for Australian Patent Application No. 2019352571, dated Dec. 19, 2024, 5 pages.

Evangeliou, Athanasios, et al.; "Branched Chain Amino Acids as Adjunctive Therapy to Ketogenic Diet in Epilepsy: Pilot Study and Hypothesis"; Journal of Child Neurology, vol. 24 No. 10; Oct. 2009; 5 pages.

\* cited by examiner

LEUCINE-ENRICHED KETOGENIC FORMULATIONS

CROSS REFERENCES TO RELATED APPLICATIONS

This application is a continuation of International Patent Application No. PCT/IB2019/001126, filed on Oct. 2, 2019, and claims priority to U.S. Patent Application No. 62/741,506, filed on Oct. 4, 2018, both of which are incorporated herein by reference in their entireties.

BACKGROUND OF THE INVENTION

Field of the Invention

Intractable epilepsy is a disorder characterized by persistent seizures that do not respond to pharmaceutical intervention with antiepileptic drugs (AEDs). A ketogenic diet (KD) is an alternative therapeutic option for patients with intractable epilepsy. However, some patients' symptoms do not completely resolve on a ketogenic diet alone.

SUMMARY OF THE INVENTION

Aspects of the disclosure relate to compositions and methods for dietary management of a subject having epilepsy, for example intractable epilepsy (also referred to as refractory epilepsy). The disclosure is based in part, on certain compositions, for example ketogenic compositions, comprising a protein source that includes a non-casein protein, leucine-enriched amino acid mixtures, and combinations thereof. In some embodiments, ketogenic compositions described by the disclosure enhance leucine availability, protein synthesis, and/or glutamate dehydrogenase expression, activity, or availability in a subject (e.g., a subject in a state of ketosis). In some embodiments, leucine-enriched amino acid mixtures (e.g., leucine-enriched essential amino acid mixtures) described by the disclosure reduce certain cellular responses associated with epileptic seizures (e.g., pyramidal cell bursting) and are therefore useful for enhancing the effect of ketogenic diets on reducing or inhibiting seizures in a subject.

In some aspects, the disclosure provides a ketogenic composition comprising: fat, a protein source, and carbohydrate, wherein: (a) the fat provides 60-90% of total calories of the composition and medium chain triglycerides (MCTs) provide between 10-40% of total calories of the composition; (b) the protein source comprises a non-casein protein and a leucine-enriched essential amino acid mixture; (c) and the ratio of calories fat to calories combined protein and net carbohydrate ranges from about 2:1 to about 4:1.

In some embodiments, a protein source comprises a non-casein protein isolate, a non-casein protein concentrate, a non-casein protein hydrolysate, or a combination of the foregoing. In some embodiments, a protein source is nutritionally complete. In some embodiments, a non-casein protein isolate is nutritionally complete. In some embodiments, a non-casein protein concentrate is nutritionally complete. In some embodiments, a non-casein protein hydrolysate is nutritionally complete. In some embodiments, a ketogenic composition is nutritionally complete.

In some embodiments, a whey protein isolate is caseinoglycomacropeptide (cGMP).

In some embodiments, a leucine-enriched essential amino acid mixture consists of L-leucine, L-histidine, L-isoleucine, L-lysine, L-methionine, L-phenylalanine, L-threonine, L-tryptophan, and L-valine.

In some embodiments, a leucine-enriched essential amino acid mixture comprises leucine at a molar ratio between 30% and 70% with respect to total essential amino acids in the mixture. In some embodiments, a leucine-enriched essential amino acid mixture comprises leucine at a molar ratio between 35% and 60% with respect to total essential amino acids in the mixture.

In some embodiments, each of the essential amino acids in a composition is present at the following molar composition ratio (%) with respect to total of essential amino acids in the composition: 0.0% to 5% of L-histidine, 5.0% to 15% of L-isoleucine, 25% to 70% of L-leucine, 8.0% to 25% of L-lysine, 2.0% to 10% of L-methionine, 2.5% to 8.0% of L-phenylalanine, 7.0% to 20% of L-threonine, 5.0% to 15% of L-valine, and 0.0% to 4.0% of L-tryptophan.

In some embodiments, the molar ratio of leucine to isoleucine in the composition ranges from about 1:1 to 4:1, the ratio of leucine to valine ranges from about 1:1 to about 4:1, or molar ratio of leucine to isoleucine in the composition ranges from about 1:1 to 4:1, the ratio of leucine to valine ranges from about 1:1 to about 4:1. In some embodiments, the molar ratio of leucine to isoleucine in the composition ranges from about 3:1 to 4:1, the ratio of leucine to valine ranges from about 3:1 to about 4:1, or the molar ratio of leucine to isoleucine in the composition ranges from about 3:1 to 4:1 and the molar ratio of leucine to valine ranges from about 3:1 to about 4:1.

In some embodiments, a leucine-enriched essential amino acid mixture consists of the composition set forth in Table 1.

In some embodiments, fat comprises about 40% to about 50% MCTs by weight.

In some embodiments, a ketogenic composition further comprises one or more vitamins and one or more minerals. In some embodiments, the one or more vitamins comprise vitamin D, vitamin K1, and/or vitamin K2. In some embodiments, the one or more minerals comprise calcium, magnesium, and/or phosphorous.

In some embodiments, a ketogenic composition has a caloric density between about 0.5 kcal/mL and about 3.35 kcal/mL, such as 1.0-2.0 kcal/mL. In specific embodiments, the composition has a caloric density of about 1.4 kcal/mL to about 1.5 kcal/mL. In some embodiments, a ketogenic composition further comprises an (one or more; at least one) emulsifier, an (one or more; at least one) antioxidant, and/or a (one or more; at least one) chelating agent.

In some embodiments, a ketogenic composition described herein has a potential renal acid load (PRAL) of less than or equal to zero. A ketogenic composition having a zero or negative PRAL reduces the risk of ketoacidosis.

In some embodiments, a ketogenic composition is a solid, optionally wherein the solid is a powder. In some embodiments, a ketogenic composition is a liquid, for example an aqueous (e.g., water-based) liquid. In some embodiments, a liquid ketogenic composition is produced by combining a solid, such as a powdered form of the ketogenic composition, with a liquid, such as water or juice. The resulting liquid ketogenic composition is administered to a subject.

In some aspects, the disclosure relates to methods of managing intractable epilepsy in a subject in need thereof. In some embodiments, the subject is (or has been determined to be) refractory to 1) antiepileptic drugs (AEDs), 2) a ketogenic diet (KD), or 3) a combination of AEDs and the KD. Without wishing to be bound by any theory, ketogenic compositions described by the disclosure, in some embodiments, stimulate protein synthesis and anabolism in a subject and/or increase the expression, activity, or availability of glutamate dehydrogenase in the subject (e.g., a subject in a state of ketosis).

Accordingly, in some aspects, the disclosure provides a method for dietary management of intractable epilepsy in a subject comprising administering to the subject an effective amount of a ketogenic composition as described by the disclosure.

In some embodiments, a subject is following or has previously followed a ketogenic diet (e.g., the subject is currently in a state of ketosis). In some embodiments, a subject has been determined to be refractory to treatment with anti-epileptic drugs (AEDs).

In some aspects, the disclosure provides a method for reducing epileptic seizures in a subject, the method comprising administering to the subject a leucine-enriched amino acid mixture comprising L-leucine, L-histidine, L-isoleucine, L-lysine, L-methionine, L-phenylalanine, L-threonine, L-tryptophan, and L-valine, wherein the leucine is present at a molar ratio between 30% and 70% with respect to total essential amino acids in the mixture; and the molar ratio of leucine to isoleucine ranges from about 1:1 to 4:1 and/or the ratio of leucine to valine ranges from about 1:1 to about 4:1.

In some aspects, the disclosure provides a method for reducing epileptic seizures in a subject, the method comprising administering to the subject a leucine-enriched essential amino acid mixture consisting of L-leucine, L-histidine, L-isoleucine, L-lysine, L-methionine, L-phenylalanine, L-threonine, L-tryptophan, and L-valine, wherein the leucine is present at a molar ratio between 30% and 70% with respect to total essential amino acids in the mixture; and the molar ratio of isoleucine ranges from about 1:1 to 4:1 and/or the ratio of leucine to valine ranges from about 1:1 to about 4:1.

In some embodiments, a subject is in a ketogenic state. In some embodiments, a subject has previously been administered a ketogenic formula or is currently following a ketogenic diet.

In some embodiments, a leucine-enriched essential amino acid mixture accounts for between about 1.0% and about 6.0% of the subject's daily caloric intake.

In some embodiments, a subject has been determined to be refractory to treatment with anti-epileptic drugs (AEDs).

In some aspects the disclosure provides a leucine enriched amino acid mixture (e.g., a leucine-enriched essential amino acid mixture) as described herein for use in a method of treating a disease or disorder characterized by a therapeutically beneficial response to ketogenic diet therapy.

In some embodiments, the disease or disorder is selected from traumatic brain injury, Autism spectrum disorder, neurodegenerative disease, for example Alzheimer's disease, cancer, metabolic conditions such as obesity and diabetes, and diseases arising from inborn errors of metabolism. In some embodiments, the diseases arising from inborn errors of metabolism are selected from glucose transporter syndrome, for example glucose transporter type 1 deficiency syndrome (Glut-1 DS), and pyruvate dehydrogenase deficiency (PDH). In some embodiments, the cancer is selected from brain tumors, for example malignant glioblastomas. In some embodiments, the disease or disorder is epilepsy. In some embodiments, leucine amino acid mixture (e.g., a leucine-enriched amino acid mixture) is administered as an athletic supplement.

In some aspects, the disclosure provides a leucine-enriched amino acid mixture (e.g., a leucine-enriched essential amino acid mixture) as described herein for use in a method for treating epilepsy in a subject. In some embodiments, the method reduces epileptic seizures in the subject.

In some embodiments, the epilepsy is intractable epilepsy (also referred to as refractory epilepsy). In some embodiments, the intractable epilepsy is intractable childhood epilepsy. In some embodiments, the subject is refractory to treatment with one or more AEDs.

In some embodiments, the subject has previously been administered a ketogenic formula or is currently following a ketogenic diet. In some embodiments, the subject is in a ketogenic state.

In some aspects, the disclosure provides a leucine-enriched essential amino acid mixture as described herein for use in clinical dietary management of a disease or disorder of a subject on a ketogenic diet.

In some aspects, the disclosure provides a leucine-enriched amino acid mixture (e.g., a leucine-enriched essential amino acid mixture) as described herein for use in a method of inducing ketosis in a subject. In some embodiments, the method further comprises administering a ketogenic diet to the subject.

In some aspects, the disclosure provides a non-therapeutic method of inducing ketosis in a subject comprising administering a leucine-enriched essential amino acid mixture as described herein to a subject. In some embodiments, the method further comprises administering a ketogenic diet to the subject.

DETAILED DESCRIPTION

Figure 1:
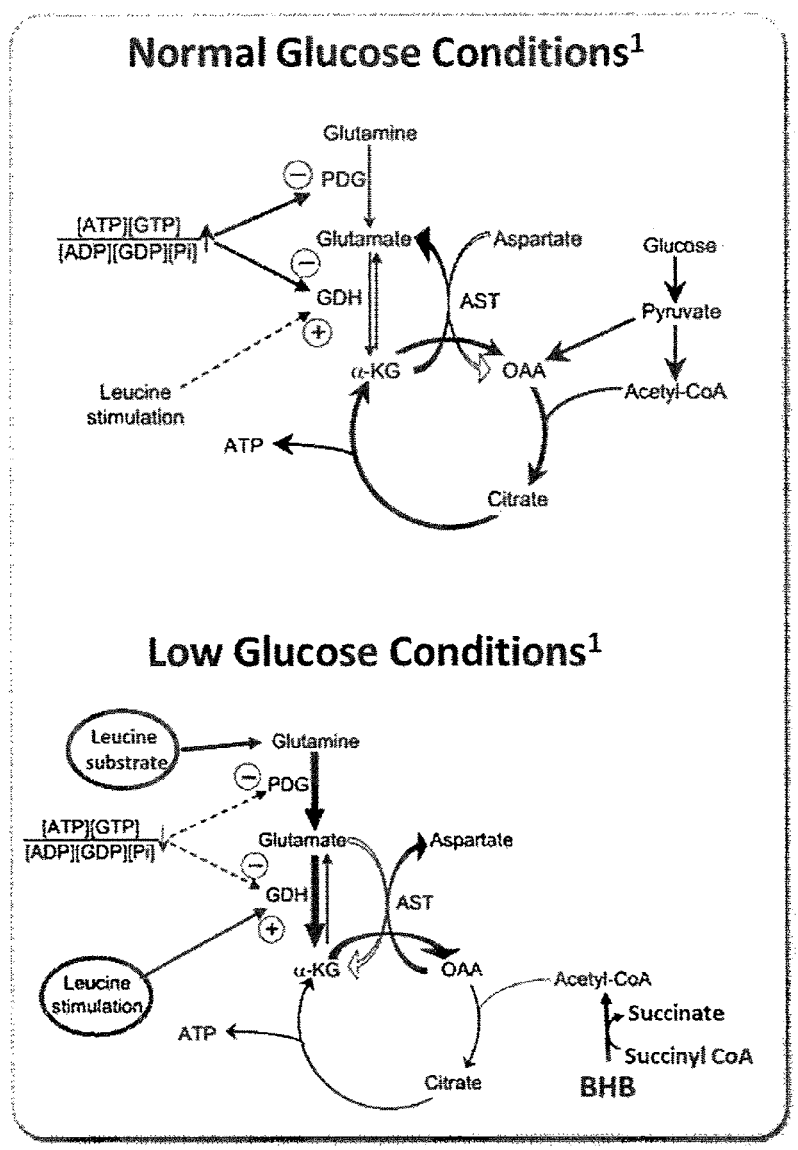
FIG. 1 is a schematic showing effects of glucose on the pathways of glutaminolysis and leucine-stimulated insulin secretion, under normal (top) and low (bottom) glucose conditions, for example as disclosed in Li et al. (2003) *Journal of Biological Chemistry*, 278(5):2853-2858. Under low glucose conditions, glutamate dehydrogenase (GDH) is responsive to allosteric stimulation by leucine, as shown by the solid line.

Aspects of the disclosure relate to compositions and methods for dietary management of a disease or condition treatable by a high fat, low carbohydrate-based ketogenic diet. The disclosure is based, in part, on ketogenic compositions comprising a protein source that includes a non-casein protein and a leucine-enriched amino acid mixture (e.g., a leucine-enriched essential amino acid mixture). In some embodiments, ketogenic compositions described by the disclosure increase the bioavailability of leucine for use in the TCA cycle (in a cell or subject), thereby stimulating or enhancing ATP production under conditions characterized by low glucose availability.

As used herein, a "ketogenic composition" refers to a composition that, when ingested by a subject for a period of time, induces a state of ketosis (elevated levels of ketone bodies in the blood) in an individual, such as a human.

In some aspects, the disclosure provides a ketogenic composition comprising: fat, a protein source, and carbohydrate, wherein: (a) the fat provides at 60-90% of total calories of the composition and medium chain triglycerides (MCTs) provide between 10-40% of total calories of the composition; (b) the protein source comprises a non-casein protein and a leucine-enriched essential amino acid mixture; (c) and the ratio of calories fat to calories combined protein and net carbohydrate ranges from about 2:1 to about 4:1.

The caloric content of a ketogenic composition can vary. In some embodiments, a ketogenic composition has a caloric density between about 0.5 kcal/mL and about 3.35 kcal/mL (e.g., about 0.5, 1.0, 1.5, 2.0, 2.5, 3.0 kcal/mL, etc.), such as 1.0-2.0 kcal/mL. In specific embodiments, the composition has a caloric density of about 1.4 kcal/mL to about 1.5 kcal/mL.

Aspects of the disclosure relate to leucine-enriched essential amino acid mixtures which reduce (e.g., suppress or inhibit) certain cellular responses associated with epileptic seizures (e.g., pyramidal cell bursting). Accordingly, in some embodiments, leucine-enriched amino acid mixtures are administered to certain subjects (e.g., subjects having or at risk of having epilepsy) to enhance the effect of ketogenic diets on reducing or inhibiting seizures.

Protein Source

Aspects of the disclosure relate to ketogenic compositions comprising a protein source. Generally, a "protein source" may comprise one type of protein or a combination of more than one type of protein. In some aspects, the disclosure provides a ketogenic composition comprising a protein source that includes a non-casein protein and a leucine-enriched essential amino acid mixture.

In some embodiments, a protein source lacks protein comprising or derived from casein. Casein is a phosphoprotein that is a component of milk which has been observed to cause allergic reactions in some subjects. A "non-casein" protein is a protein or protein preparation (e.g., protein isolate, protein concentrate, protein hydrolysate, etc.) that lacks casein. In some embodiments, a protein source comprises a non-casein protein isolate, a non-casein protein concentrate, a non-casein protein hydrolysate, or a combination of the foregoing. In some embodiments, a non-casein protein is derived from a source that contains casein (e.g., milk) but that has been purified to remove the casein.

In some embodiments, a non-casein protein is whey protein (or a whey protein preparation, such as an isolate, concentrate, or hydrolysate). In some embodiments, a whey protein isolate is caseino-glycomacropeptide (cGMP).

In some embodiments, a protein source is nutritionally complete. As used herein "nutritionally complete" protein refers to a protein that contains an adequate proportion of each of the nine essential amino acids necessary in the human diet (e.g., an adequate proportion of L-leucine, L-histidine, L-isoleucine, L-lysine, L-methionine, L-phenylalanine, L-threonine, L-tryptophan, and L-valine). In some embodiments, a non-casein protein isolate is nutritionally complete. In some embodiments, a non-casein protein concentrate is nutritionally complete. In some embodiments, a non-casein protein hydrolysate is nutritionally complete.

In some embodiments, a ketogenic composition is nutritionally complete. As used herein, a "nutritionally complete" ketogenic composition refers to a composition that provides 100% of the recommend values (for a subject) of carbohydrates, protein, fat, vitamins, and minerals and can be used on its own as a sole source of nutrition.

Aspects of the disclosure relate to leucine-enriched amino acid mixtures (e.g., leucine-enriched essential amino acid mixtures). Leucine-enriched amino acid mixtures described herein may be administered to a subject alone (e.g., as a powder, solid, gel, aqueous solution, etc. that does not contain any other active ingredients) or as part of a composition, such as a ketogenic composition or other foods or formulas. For example, compositions comprising a leucine-enriched amino acid mixture (e.g., a leucine-enriched essential amino acid mixture) may comprise additional components, such as solubilizing agents, flavorings, stabilizers, etc.

In some embodiments, a leucine-enriched amino acid mixture is provided to a subject in order to supplement the subject's nutritional needs (e.g., in order to supplement the ketogenic diet of the subject). "Ketogenic diet" generally refers to a diet comprising a certain ratio (e.g., 4:1, 3:1, 2.5:1, etc.) of fat to protein and carbs, that is consumed by a subject in order to promote ketosis in the subject. In some embodiments, a ketogenic diet is prescribed to a subject for the purpose of reducing epileptic seizures.

As used herein, "leucine-enriched amino acid mixture" refers to a composition comprising several amino acids in elemental (e.g., individual) form that contains a higher proportion (e.g., as measured by percent molar concentration in the mixture) of L-leucine relative to any of the other individual amino acids. In some embodiments, a leucine-enriched amino acid mixture comprises of L-leucine, L-histidine, L-isoleucine, L-lysine, L-methionine, L-phenylalanine, L-threonine, L-tryptophan, and L-valine. In some embodiments, a leucine-enriched amino acid mixture consists of L-leucine, L-histidine, L-isoleucine, L-lysine, L-methionine, L-phenylalanine, L-threonine, L-tryptophan, and L-valine, and is referred to as a "leucine-enriched essential amino acid mixture".

In some embodiments, a leucine-enriched amino acid mixture (e.g., a leucine-enriched essential amino acid mixture) comprises leucine at a molar ratio between 30% and 70% (e.g., about 30%, about 35%, about 40%, about 45%, about 50%, about 55%, about 60%, about 65%, or about 70%) with respect to total essential amino acids in the mixture. In some embodiments, a leucine-enriched essential amino acid mixture comprises leucine at a molar ratio between 35% and 60% (e.g., 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60%) with respect to total essential amino acids in the mixture.

In some embodiments, each of the amino acids in a composition is present at the following molar composition ratio (%) with respect to total of essential amino acids in the composition: 0.0% to 5% (e.g., about 0.1%, about 0.5%, about 1%, about 2%, about 3% about 4% or about 5%) of L-histidine, 5.0% to 15% (e.g., about 5%, about 6%, about 7%, about 8%, about 9% about 10%, about 11%, about 12% about 13%, about 14%, or about 15%) of L-isoleucine, 25% to 70% (e.g., about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70%) of L-leucine, 8.0% to 25% (e.g., about 8%, about 9% about 10%, about 11%, about 12% about 13%, about 14%, about 15%, about 16%, about 17%, about 18%, about 19%, about 20%, about 21%, about 22% about 23% about 24%, or about 25%) of L-lysine, 2.0% to 10% of L-methionine (e.g., about 2%, about 3% about 4%, about 5%, about 6%, about 7%, about 8%, about 9%, or about 10%), 2.5% to 8.0% (e.g., about 2.5%, about 3%, about 4%, about 5%, about 6%, about 7%, or about 8%) of L-phenylalanine, 7.0% to 20% (e.g., about 7, about 8%, about 9% about 10%, about 11%, about 12% about 13%, about 14%, about 15%, about 16%, about 17%, about 18%, about 19%, or about 20%) of L-threonine, 5.0% to 15% (e.g., about 5%, about 6%, about 7%, about 8%, about 9% about 10%, about 11%, about 12% about 13%, about 14%, or about 15%) of L-valine, and 0.0% to 4.0% (e.g., about 0.1%, about 0.5%, about 1%, about 2%, about 3%, or about 4%) of L-tryptophan.

In some embodiments, the molar ratio of leucine to isoleucine in the composition ranges from about 1:1 to 4:1 (e.g., 1:1, 1.5:1, 2:1, 2.5:1, 3:1, 3.5:1, 4:1, etc.), the ratio of leucine to valine ranges from about 1:1 to about 4:1 (e.g., 1:1, 1.5:1, 2:1, 2.5:1, 3:1, 3.5:1, 4:1, etc.), or a combination of the foregoing. In some embodiments, the molar ratio of leucine to isoleucine in the composition ranges from about 3:1 to 4:1, the ratio of leucine to valine ranges from about 3:1 to about 4:1, or a combination of the foregoing.

In some embodiments, a leucine-enriched amino acid mixture consists of about 39.32% Leucine, 18.53% Lysine (e.g. Lysine Acetate), 10.81% valine, 10.46% isoleucine, 9.11% Threonine, 6.62% Phenylalanine, 3.21% Methionine, 1.24% Histidine, and 0.69% Tryptophan. In some embodiments, a leucine-enriched essential amino acid mixture consists of (per 5 g): 1.9660 g Leucine, 0.9265 g Lysine (e.g., lysine acetate), 0.5405 g Valine, 0.5230 g Isoleucine, 0.4555 g Threonine, 0.3310 g Phenylalanine, 0.1605 g Methionine, 0.0620 g Histidine, and 0.0345 g Tryptophan.

An adverse effect of some ketogenic compositions is ketoacidosis. In order to reduce the risk of acidosis, proteins generating lower amounts of acidic metabolites are utilized in the compositions described herein. Potential renal acid load (PRAL) is a method used to quantify the acidity of foods. A positive PRAL score indicates an acid forming food. A negative PRAL score indicates an alkaline-forming food. In some embodiments, the protein used in the compositions described herein have a PRAL score less than or equal to zero. In some embodiments, the ketogenic composition has a PRAL score that is less than or equal to zero.

The protein may also affect the emulsion stability of the compositions (e.g., liquid compositions) described herein. In some embodiments, a liquid ketogenic composition described herein comprises a protein that interacts with lipid in the composition to form a stable emulsion.

Fats

The majority of calories in a ketogenic composition are derived from fat. Examples of fat sources include but are not limited to: butter, animal fat (for example, beef fat or chicken fat), vegetable oil (for example, avocado, corn, and soybean), olive oil, canola oil, coconut oil, cocoa butter, fish oil, nuts (for example, macadamia and peanut), and nut oils.

In some embodiments, fat provides between about 60% and about 90% of the calories present in a ketogenic composition described herein. In some embodiments, fat provides at least 70% of the calories present in a ketogenic composition. In some embodiments, fat provides at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, or at least 90% of the calories present in the ketogenic composition.

The fat can be a single fat or multiple (two or more), different fats. The fat of the ketogenic compositions described herein may comprise saturated fats, unsaturated fats, or a combination of saturated fats and unsaturated fats. Fat can comprise long chain fatty acids, short chain fatty acids or a combination of long chain fatty acids and short chain fatty acids. In some embodiments, fat comprises triglycerides, such as short-chain triglycerides, long-chain triglycerides, medium-chain triglycerides, or a combination of two or three of the foregoing (e.g., short-chain triglycerides, long-chain triglycerides, and medium-chain triglycerides; short-chain triglycerides and long-chain triglycerides; short-chain triglycerides and medium-chain triglycerides; medium-chain triglycerides and long-chain triglycerides).

Fat in the ketogenic composition can comprise a combination of MCTs and fat from one or more oil, such as from nuts, seeds or nuts and seeds. From about 1 grams to about 50 grams MCTs can be included per liter composition (e.g., about any of 1, 2, 3, 4, 5, 10 15, 20, 25, 30, 35, 40, 45 or 50 grams MCTs or any number of grams within the range). From about 100 grams to about 150 grams fat from one or more oils, such as oils from nuts, seeds or a combination of nuts and seeds, can be included per liter composition (e.g., about any of 100, 105, 110, 115, 120, 125, 130, 135, 140, 145 or 150 grams fat from one or more oils or any number of grams within the range).

In some embodiments, fat comprises between about 1% and about 50% medium chain triglycerides (MCT). In some embodiments, fat comprises between about 10% and about 30% calories from medium chain triglycerides. In some embodiments, fat comprises about 20%, about 21%, about 22%, about 23%, about 24%, about 25%, about 26%, about 27%, about 28%, about 29%, or about 30% calories from medium chain triglycerides. In some embodiments, the total fat comprises at least 10% calories from medium chain triglycerides (MCTs). In some embodiments, the total fat comprises at least 25% calories MCTs. In some embodiments, a chelating agent, such as sodium hexametaphosphate (SHMP), chelates minerals in the composition and helps reduce fat rancidity. In some embodiments, a ketogenic composition further comprises docosahexaenoic acid (DHA).

Emulsifiers

Emulsifiers can be used to improve stability and texture of ketogenic compositions (e.g., liquid ketogenic compositions) described herein. In some aspects, ketogenic compositions comprise an emulsifier or emulsifying agent (e.g., a surfactant), such as sodium stearoyl lactylate (SSL), lecithin, starches, gums, and biopolymeric emulsifiers. In some embodiments, the emulsifier is sodium stearoyl lactylate (SSL). In some embodiments, the emulsifier is a modified starch, such as octenyl succinate starch or other modified starch, that interferes with interaction of fat and protein in the composition, such as by binding of the octenyl moiety of the starch to fat globules. Without wishing to be bound by theory, binding of the modified starch to fat interferes (totally or partially) by steric hindrance with interaction of fat with proteins.

Emulsifier in a ketogenic composition can comprise one type of emulsifier or a combination of more than one (e.g., 2, 3, 4, 5, or more) type(s) of emulsifier. In some embodiments, the emulsifier is sodium steroyl lactolate (SSL). From about 0.5 grams to about 2 grams emulsifier (e.g., SSL) can be included per liter composition (e.g., about any of 0.5, 0.6, 0.7, 0.8, 0.9, 1, 1.1, 1.2, 1.3, 1.4, 1.5, 1.6, 1.7, 1.8, 1.9, or 2 grams emulsifier (e.g., SSL) or any number of grams within the range).

Vitamins and Minerals

A ketogenic composition described herein may further comprise vitamins and minerals. In some embodiments, a ketogenic composition comprises at least one vitamin selected from the group consisting of Vitamin A, Vitamin B1, Vitamin B2, Vitamin B3, Vitamin B5, Vitamin B6, Vitamin B12, folic acid, Vitamin C, choline, Vitamin D, Vitamin E, and Vitamin K1 and Vitamin K2. Sources of vitamins include: palmitates, beta-carotene, ergocalciferol, cholecalciferol, dl-alpha tocopheryl acetate, d-alpha tocopheryl acetate, dl-alpha tocotrienols, calcium panthothenate, pantothenol, pantothenic acid, cyanocobalamin, methylcobalamin, sodium ascorbate, calcium ascorbate, ascorbic acid, pyridoxine hydrochloride, pyridoxal 5'phosphate, riboflavin, thiamin, folic acid, phylloquinone, phytomenadione, phytonadione, menaquinones (e.g., MK-4 and MK-7) and biotin. Any combination of vitamins can be included in a ketogenic composition.

In some embodiments, a ketogenic composition comprises at least one mineral selected from the group consisting of: calcium, phosphorus, choline, magnesium, zinc, manganese, iron, copper, chromium, chloride, potassium, iodine, selenium, molybdenum and sodium. Sources of minerals include: calcium lactate, calcium gluconate, calcium pantothenate, calcium lactate gluconate, calcium phosphate, calcium carbonate, calcium citrate, calcium phosphate, magnesium phosphate, potassium phosphate, choline chloride, phosphatidylcholine, choline bitartrate, lecithin, magnesium chloride, magnesium oxide, magnesium gluconate, magnesium phosphate, magnesium malate, magnesium citrate, inositol hexanicotinate, nicotinamide, niacinamine, zinc carbonate, zinc citrate, zinc sulfate, zinc gluconate, zinc bisglycinate, manganese chloride, manganese gluconate, manganese sulfate, manganese picolinate, iron sulfate, iron citrate, iron gluconate, cupric oxide, copper gluconate, copper sulfate, copper carbonate, chromium picolinate, chromium chloride, chromium polynicotinate, chromium chloride, sodium chloride, potassium chloride, magnesium chloride, manganese chloride, choline chloride, potassium chloride, potassium citrate, potassium iodide, potassium sodium tartrate, potassium bisulfite, potassium iodide, sodium selenite, selenomethionine, sodium selenite, potassium molybdate, sodium molybdate, sodium chloride and sodium citrate.

In some embodiments, a ketogenic composition further comprises carnitine. Sources of carnitine include L-carnitine L-tartrate, L-carnitine citrate and L-carnitine acetate. In some embodiments, the composition comprises between about 0.2 mg and about 100 mg carnitine per 100 mL or between about 45 mg and 55 mg carnitine per 100 mL. In some embodiments, the composition comprises between about 30 mg and about 60 mg carnitine per 100 mL.

The addition of certain minerals, such as zinc, copper and/or iron, to food products is known to contribute to fat rancidity in food products. Chelation of sensitive minerals may therefore reduce fat rancidity by preventing minerals associated with fat rancidity from interacting with fats that are present in a composition. In some embodiments, a ketogenic composition comprises a chelating agent, such as phosphates or phosphonates, EDTA and sodium hexametaphosphate (SHMP). In some embodiments, the chelating agent is sodium hexametaphosphate (SHMP). Other methods of reducing fat rancidity, such as the addition of antioxidants, are also known in the art. In some embodiments, the ketogenic composition described herein comprises at least one antioxidant, such as ascorbate, ascorbic acid (Vitamin C), cysteine and tocopherols.

Chelating agent in a ketogenic composition can comprise one type of chelating agent or a combination of more than one type of chelating agent. In some embodiments, the chelating agent is sodium hexametaphosphate (SHMP). From about 1 gram to about 2 grams chelating agent (e.g., SHMP) can be included per liter composition (e.g., any of about 1, 1.1, 1.2, 1.3, 1.4, 1.5, 1.6, 1.7, 1.8, 1.9 or 2 grams chelating agent (e.g., SHMP) or any number of grams within the range).

Carbohydrates

Carbohydrate in a ketogenic composition can comprise one type of fiber or a combination of more than one type of fiber (e.g., a fiber blend). From about 15 grams to about 25 grams fiber can be included per liter of composition (e.g., any of about 15, 16, 17, 18, 19, 20, 21, 22, 23, 24 or 25 grams fiber or any number within the range).

Carbohydrate in the composition can comprise one type of fiber or a combination of more than one type of fiber (e.g., a fiber blend). From about 18 grams to about 22 grams fiber can be included per liter of composition (e.g., any of about 18, 18.5, 19, 19.5, 20, 20.5, 21, 21.5 or 22 grams fiber or any number within the range).

In some embodiments, the fiber is dietary fiber. In some embodiments, the fiber is a combination of dietary fibers. In some embodiments, the dietary fibers are soluble fibers, non-soluble fibers, or dietary fibers and non-soluble fibers. In some embodiments, the fiber comprises very low density lipoprotein (vldl)- and low density lipoprotein (ldl)-reducing soluble fibers. In some embodiments, the fiber is one or more selected from the group consisting of inulin, pectin, cellulose gum (carboxymethyl cellulose) and carrageenan. Fiber can be useful in the treatment or prevention of constipation, which is a common and unpleasant side effect of consumption of ketogenic compositions.

In some embodiments, a composition (e.g., a ketogenic composition, a leucine-enriched amino acid composition, etc.) further comprises at least one sweetener, such as acesulfame potassium, sucralose, aspartame, lo han guo, stevia, erythritol, xylitol, maltitol, sorbitol, and other nutritive or non-nutritive sources. Sweetener in the composition can comprise one type of sweetener or a combination of more than one type of sweetener. A sweetener can be a nutritive sweetener (e.g., glucose), or a non-nutritive sweetener (e.g., stevia). From about 0 grams (no added) to about 10 grams sweetener can be included per liter of composition (e.g., any of about 0, 1, 2, 3, 4, 5, 6, 7, 8, 9 or 10 grams sweetener or any number within the range).

Methods

In some aspects, the disclosure relates to ketogenic compositions that, in some embodiments, stimulate ATP production in the mitochondria in low glucose conditions. The disclosure is based, in part, on leucine-enriched amino acid mixtures and/or ketogenic compositions which have amino acid ratios that enhance anaplerosis and/or the amount or availability of certain TCA cycle substrates. Thus, aspects of the disclosure relate to compositions and methods for dietary management of a subject having a disease or disorder characterized by symptomatic improvement upon treatment by the ketogenic diet.

Additional diseases characterized by clinical response to ketogenic diet therapy include but are not limited to traumatic brain injury (TBI), neurodegenerative disease (e.g., Alzheimer's disease), some cancers (e.g., brain tumors, malignant glioblastomas), metabolic conditions (e.g., obesity, diabetes) and diseases related to certain inborn errors of metabolism (e.g., glucose transporter syndrome and pyruvate dehydrogenase deficiency).

In some aspects, the disclosure relates to methods of managing intractable epilepsy in a subject in need thereof. As used herein, a subject having "intractable epilepsy" refers to a subject with epilepsy that is refractory to treatment with one or more therapeutics, for example one or more antiepileptic drugs (AEDs) (e.g., 2, 3, 4, 5, or more AEDs), for example as described by Sinha et al. Neurosciences (Riyadh). 2011 January; 16(1):3-9 and/or a ketogenic diet (KD).

In some aspects, the disclosure provides methods of inhibiting epileptic seizures (e.g., inhibiting certain cellular responses associated with epileptic seizures, such as pyramidal cell bursting) by administering a composition as described by the disclosure, for example a leucine-enriched amino acid mixture (e.g., a leucine-enriched essential amino acid mixture) or a ketogenic composition. In some embodiments, pyramidal cell bursting is reduced in the cells of a subject administered a leucine-enriched amino acid mixture by about 5%, 10%, 15%, 20%, 25%, 30%, 35%, 40%, 45%, 50%, 55%, 60%, 65%, 70%, 75%, 80%, 85%, 90%, 95%, 99%, or more relative to a subject that has not been administered the mixture (e.g., a subject only following a ketogenic diet).

In some embodiments, epileptic seizure occurrence is reduced in a subject who has been administered a leucine-enriched amino acid mixture (e.g., a leucine-enriched essential amino acid mixture) by about 5%, 10%, 15%, 20%, 25%, 30%, 35%, 40%, 45%, 50%, 55%, 60%, 65%, 70%, 75%, 80%, 85%, 90%, 95%, 99%, or more relative to a subject that has not been administered the mixture (e.g., a subject only following a ketogenic diet). In some embodiments, the subject experiences a reduction of 1, 2, 3, 4, 5, 6, 7, 8, 9, 10, or more than 10 seizures in a given time period (e.g., per day, per week, per month, per year, etc.). In some embodiments, a subject that has been administered a composition (e.g., a ketogenic composition and/or a leucine-enriched essential amino acid mixture) experiences a reduction in severity of epileptic seizures relative to the severity of seizures experienced by the subject prior to the administration. In some embodiments, the subject ceases to experience epileptic seizures after administration of the composition.

A subject can be any mammal. In some embodiments, a subject is a human. The age of a subject can vary. In some embodiments, a subject is an infant (e.g., a subject between the ages of 1 day old and 12-months old). In some embodiments, a subject is a juvenile (e.g., between 1 year old and 18 years old). In some embodiments, a subject is an adult (e.g., between 18 years old and 60 years old). In some embodiments, a subject is geriatric (e.g., at least 60 years old).

Examples of AEDs include but are not limited to Acetazolamide, Acetazolam, Carbamazepine, Tegretol, Mazepine, Carbamazepine CR, Clobazam, Frisium, Clonazepam, Rivotril, Clonpam, Clonazepam-R, Diazepam, Valium, Diastat, Diazemuls, Dipam, Ethosuximide, Zarontin, Fosphenytoin, Cerebyx, Gabapentin, Neurontin, Lacosamide, Vimpat, Lamotrigine, Lamictal, Levetiracetam, Keppra, Lorazepam, Ativan, Loraz, Methsuximide, Celontin, Nitrazepam, Mogadon, Nitrazedon, Oxcarbazepine, Trileptal, Paraldehyde, Phenobarbital, Phenobarb, Phenobarbital Sodium, Phenytoin, Dilantin, Phenytoin Sodium, Tremytoine, Pregabalin, Lyrica, Primidone, Rufinamide, Banzel, Stiripentol, Diacomit, Topiramate, Topamax, Valproic Acid, Epival, Depakene, Divalproex Sodium, Sodium Valproate, Vigabatrin, Sabril, Felbamate (Felbatol), Tiagabine Hydrochloride (Gabitril), and Zonisamide (Zonegran).

The terms "intractable epilepsy" and "refractory epilepsy" generally means that a subject 1) continues to experience seizures (e.g., the number of seizures experienced by the patient is not reduced in number over a given period of time, such as per day) after treatment with one or more AEDs, 2) continues to experience seizures (e.g., the number of seizures experienced by the patient is not reduced in number over a given period of time, such as per day) by following a ketogenic diet, or 3) continues to experience seizures (e.g., the number of seizures experienced by the patient is not reduced in number over a given period of time, such as a day) after treatment with a combination of one or more AEDs and following a ketogenic diet.

In some embodiments, the subject is (or has been determined to be) refractory to 1) antiepileptic drugs (AEDs), 2) a ketogenic diet (KD), or 3) a combination of AEDs and the KD.

Accordingly, in some aspects, the disclosure provides a method for dietary management of intractable epilepsy (e.g., refractory epilepsy) in a subject comprising administering to the subject an effective amount of a ketogenic composition as described by the disclosure.

In some embodiments, a subject is following or has previously followed a ketogenic diet (e.g., the subject is currently in a state of ketosis). A "state of ketosis" in a subject includes a shift in the metabolism of the subject from glucose-based metabolism to metabolism of ketone bodies (e.g., beta-hydroxybutyrate (BHB), Acetoacetate (AcAc), acetone, etc.) for production of molecules such as ATP. Modalities for measuring whether a subject is in a state of ketosis are known (for example measurement of O-hydroxybutyrate (BHB) in the blood of a subject, measurement of ketones in the urine of a subject, etc.) and are described for example by Miller et al. *J Nutr Metab.* 2018; 2018: 5157645. In some embodiments, a subject in a state of ketosis is characterized by a blood concentration of BHB that is between 0.5 mmol/L to about 6.0 mmol/L. In some embodiments, a subject in a state of ketosis is characterized by a blood concentration of BHB that is between 2.5 mmol/L and 5.0 mmol/L.

Compositions described herein (e.g., ketogenic compositions, leucine-enriched amino acid mixtures, etc.) may be administered by a variety of methods, such as by tube feeding or oral delivery. In some embodiments, a ketogenic composition or leucine-enriched amino acid mixture (e.g., leucine-enriched essential amino acid mixture) is delivered by tube feeding. In some embodiments, a ketogenic composition or leucine-enriched amino acid mixture is packaged in a carton, such as a Tetra Pak, and delivered orally. In some embodiments, a ketogenic composition or leucine-enriched amino acid mixture is stored in a can, bottle or pouch.

The amount and timing for administration of a composition (e.g., a ketogenic composition, leucine-enriched amino acid mixture, etc.) can vary. In some embodiments, a subject is administered a composition once, twice, three times, four times, five times, six times, or more per day. In some embodiments, a ketogenic composition as described by the disclosure is administered as the sole source of nutrition of a subject. In some embodiments, a ketogenic composition or a leucine-enriched amino acid mixture as described by the disclosure is administered to a subject as a nutritional supplement.

The disclosure is based, in part, on the recognition that doses of leucine-enriched amino acid mixtures that are lower than previously described are effective in inhibiting seizures in a subject. Lower doses of leucine supplements are beneficial, in some embodiments, because they avoid potential issues of leucine toxicity and metabolic imbalance (e.g., imbalance of amino acids in a subject). In some embodiments, the amount of a leucine-enriched amino acid mixture administered to a subject provides an additional 0.001 g leucine per kcal (0.001 g/kcal) to about 0.009 g/kcal leucine (e.g., 0.001 g/kcal, 0.002 g/kcal, 0.003 g/kcal, 0.004 g/kcal, 0.005 g/kcal, 0.006 g/kcal, 0.007 g/kcal, 0.008 g/kcal, or 0.009 g/kcal) per day to the subject.

In some embodiments, the amount of a leucine-enriched amino acid mixture administered to a subject provides an additional 0.001 g/kcal leucine to about 0.002 g/kcal leucine per day to the subject. In some embodiments, the amount of a leucine-enriched amino acid mixture administered to a subject provides an additional 0.002 g/kcal leucine to about 0.003 g/kcal leucine per day to the subject. In some embodiments, the amount of a leucine-enriched amino acid mixture administered to a subject provides an additional 0.003 g/kcal leucine to about 0.004 g/kcal leucine per day to the subject. In some embodiments, the amount of a leucine-enriched amino acid mixture administered to a subject provides an additional 0.004 g/kcal leucine to about 0.005 g/kcal leucine per day to the subject. In some embodiments, the amount of a leucine-enriched amino acid mixture administered to a subject provides an additional 0.005 g/kcal leucine to about 0.006 g/kcal leucine per day to the subject. In some embodiments, the amount of a leucine-enriched amino acid mixture administered to a subject provides an additional 0.006 g/kcal leucine to about 0.007 g/kcal leucine per day to the subject. In some embodiments, the amount of a leucine-enriched amino acid mixture administered to a subject provides an additional 0.007 g/kcal leucine to about 0.008 g/kcal leucine per day to the subject. In some embodiments, the amount of a leucine-enriched amino acid mixture administered to a subject provides an additional 0.008 g/kcal leucine to about 0.009 g/kcal leucine per day to the subject.

In some embodiments, the amount of a leucine-enriched amino acid mixture administered to a human subject is calculated based on the amount of the mixture that has been administered to a mouse (e.g., a human equivalent dose, HED, is calculated). Methods of converting amino acid dosages from a mouse to a human (e.g., calculating a HED) are described, for example by Nair (2016) *J Basic Clin Pharma* 7:27-31.

In some embodiments, a leucine-enriched amino acid composition is administered to a human subject at an inclusion rate of between 2.0% and about 3.5% (e.g., about 2.0%, 2.5%, 3%, 3.5%, or any value there between). In some embodiments, a human subject is administered an amount of a leucine-enriched amino acid mixture sufficient to provide between about 0.03 g/kg/day and about 0.095 g/kg/day additional leucine to the subject. In some embodiments, a human subject is administered an amount of a leucine-enriched amino acid mixture sufficient to provide about 0.03, 0.04. 0.05, 0.06, 0.07, 0.08, 0.095 g/kg/day additional leucine to the subject.

In some embodiments, a subject is administered about 100 mL, 200 mL, 300 mL, 400 mL, 500 mL, 600 mL, 700 mL, 800 mL, 900 mL, or 1 L of a ketogenic composition (e.g., per administration, per day, etc.). In some embodiments, a subject is administered more than 1 L (per administration or per day) of a ketogenic composition.

Other features of the invention will become apparent in the course of the following descriptions of exemplary embodiments which are given for illustration of the invention and are not intended to be limiting thereof.

EXAMPLES

Example 1

This example describes ketogenic compositions that include a protein source comprising a non-casein, nutritionally complete protein and a leucine-enriched amino acid mixture.

KetoVie® 4:1 is a liquid ready to use prescription medical food for the clinical dietary management of intractable epilepsy, glucose transporter type 1 deficiency syndrome (Glut-1 DS), pyruvate dehydrogenase deficiency (PDH) and other disorders that require a ketogenic diet. KetoVie® 4:1 comprises the following nutritional characteristics: a non-casein protein source (e.g., whey protein), 25% of Calories from medium chain triglycerides (MCTs), nutritional completeness, carnitine, a bone health vitamin and mineral blend (e.g., added calcium, vitamin D, vitamin K1, vitamin K2, magnesium, and phosphorous), selenium, and citrates.

A Ketogenic diet (KD) is an established treatment for intractable childhood epilepsy, with seizure free rates in refractory patients reported at 16% in meta-analyses. KD has been recommended to be used after 2 anti-seizure drugs (e.g., anti-epilepsy drugs, "AEDs" have failed. A certain proportion of intractable epilepsy patients also fail to adequately respond to KD. However, there are limited therapeutic options for those patients whose epilepsy is not adequately controlled on both AEDs and KD.

The KD changes brain metabolism from glucose to ketone bodies (KBs), changing the metabolic environment. For example, under normal physiological conditions, glucose is the main energy substrate of the brain and lactate, derived from glycolysis in astrocytes and released as a function of $K^+$ and glutamate uptake, is oxidized by neurons as an activity dependent fuel after being reduced to pyruvate. In nutritional ketosis (e.g., when a subject is in a state of ketogenesis) on the other hand, KBs become a preferred energy substrate in the brain and suppress the production of lactate in astrocytes thereby making the excitatory neurotransmitter glutamate an activity-dependent fuel of choice in neurons and astrocytes. KBs have been observed to open large pannexin-1 hemichannels releasing ATP, which is reduced to the neuroprotectant adenosine and activates G-protein coupled $A_1$ receptors thereby opening $K_{ATP}$ channels via second messenger signaling and reducing neuronal hyper-excitability.

Under low glucose conditions, KBs have been observed to feed into the TCA cycle creating a need for intermediary co-factors, such as branched chain amino acids (BCAAs), for example, leucine which activates glutamate dehydrogenase enzyme and in turn converts glutamate (excitatory neurotransmitter) into alpha-ketoglutarate for energy production (FIG. 1). However, diets supplementing Leu only to a low protein diet control for prolonged periods have been observed to increase catabolism of valine and isoleucine, producing an amino acid imbalance. Furthermore, supplementing BCAAs only has been observed to deplete plasma concentrations of other essential amino acids. The disclosure is based, in part, on leucine-enriched amino acid mixtures which provide an increased TCA cycle substrates while maintaining an appropriate total amino acid balance in a subject.

KBs are oxidized to Acetyl CoA via TCA cycle intermediate succinylCoA, creating demand for α-ketogluterate via anaplerosis. TCA cycle capacity and oxidative metabolism of Glu to α-ketogluterate is mediated by glutamate dehydrogenase (GDH), which is allosterically activated by ADP and Leu. KBs are more efficient than glucose in ATP generation by increasing TCA cycle flux, resulting in higher de novo synthesis of Glu and Gln. Higher concentrations of these AAs require proteolysis and metabolism of branched-chain amino acids (BCAAs), such as leucine (Leu), which represents 50% of nitrogen content of amino acids Glu and Gln. Leu is also a potent stimulator of mTORC1 which stimulates protein, lipid and nucleotide (AMP, GMP, etc.) synthesis. Leucine augments KB activity via signaling activities for activation of Glu oxidation and mTORC1, and as a substrate for. TCA anaplerosis of key intermediates. In some embodiments, other amino acids (e.g., essential amino acids) present in leucine-enriched amino acid mixtures described herein provide additional TCA substrates via anaplerosis.

In summary, when a subject is in a ketogenic state, the brain will utilize KB as the preferred energy source. KBs feed into the TCA cycle creating a need for intermediary co-factors. Ketogenic compositions comprising leucine-enriched amino acid mixtures, in some embodiments, provide elevated amounts of leucine, which activates glutamate dehydrogenase enzyme that converts glutamate (excitatory neurotransmitter) into alpha-ketoglutarate for energy production. Without wishing to be bound by any particular theory, by providing leucine for activation of glutamate dehydrogenase, ketogenic composition comprising leucine-enriched amino acid mixtures may also be useful for treating diseases or disorders associated with treatment effect by ketogenic diet, such as traumatic brain injury (TBI), neurodegenerative disease (e.g., Alzheimer's disease), some cancers (e.g., brain tumors, malignant glioblastomas), metabolic conditions (e.g., obesity, diabetes) and diseases related to certain inborn errors of metabolism (e.g., glucose transporter syndrome and pyruvate dehydrogenase deficiency).

Example 2

This example describes evaluation of anti-epileptic potential of a ketogenic diet supplemented with a leucine-enriched amino acid composition. A rat model of epilepsy was used. Animals were placed on a ketogenic diet (KD) supplemented with either a casein-based amino acid mixture (AA), or a dose of a leucine-enriched essential amino acid composition, and the effect on epileptic seizures was measured in hippocampal slices and compared to control animals. One embodiment of a leucine-enriched amino acid composition is shown below in Table 1. One embodiment of a casein-based amino acid mixture is shown in Table 2.

TABLE 1

|   | Amino Acid | Percentage (%) | Per 1 g |
|---|---|---|---|
| 1 | L-Leu | 40.000 | 0.4 |
| 2 | L-Lys•HCl | 16.691 | 0.1669 |
| 3 | L-Val | 11.000 | 0.11 |
| 4 | L-Ile | 10.636 | 0.1064 |
| 5 | L-Thr | 9.273 | 0.0927 |
| 6 | L-Phe | 6.727 | 0.0673 |
| 7 | L-Met | 3.273 | 0.0327 |
| 8 | L-His•HCl | 1.700 | 0.017 |
| 9 | L-Trp | 0.700 | 0.007 |

TABLE 1-continued

| Amino Acid | Percentage (%) | Per 1 g |
|---|---|---|
| total (%) | 100.000 | 1.000 |

TABLE 2

| Casein composition amino acids (Total 99.6 g) | grams |
|---|---|
| His | 2.70 |
| Ile | 4.73 |
| Leu | 8.64 |
| Lys•HCl | 9.36 |
| Met | 2.58 |
| Phe | 4.78 |
| Thr | 4.04 |
| Trp | 1.15 |
| Val | 6.09 |
| Ala | 2.71 |
| Arg | 3.48 |
| Asn•H2O | 3.82 |
| Asp | 3.36 |
| Cys-Cys | 0.54 |
| Gln | 9.73 |
| Glu | 9.73 |
| Gly | 1.72 |
| Pro | 9.95 |
| Ser | 5.37 |
| Tyr | 5.15 |

Four-week old male SD rats were fed the following diets for three weeks. KD-AA diet comprises a ketogenic diet (6:1 ketogenic ratio) supplemented with 3.3% casein-based amino acids. KD-L diet comprises a ketogenic diet (6:1 ketogenic ratio) supplemented with 3.3% of a leucine-enriched essential amino acid mixture (e.g., as shown in Table 1). Note that 3.3% of the leucine-enriched amino acid mixture corresponds to 0.004465 g/kcal. The control animals were fed a CRF-1 diet (Oriental Yeast Co., Ltd., Tokyo, Japan).

Figure 2:
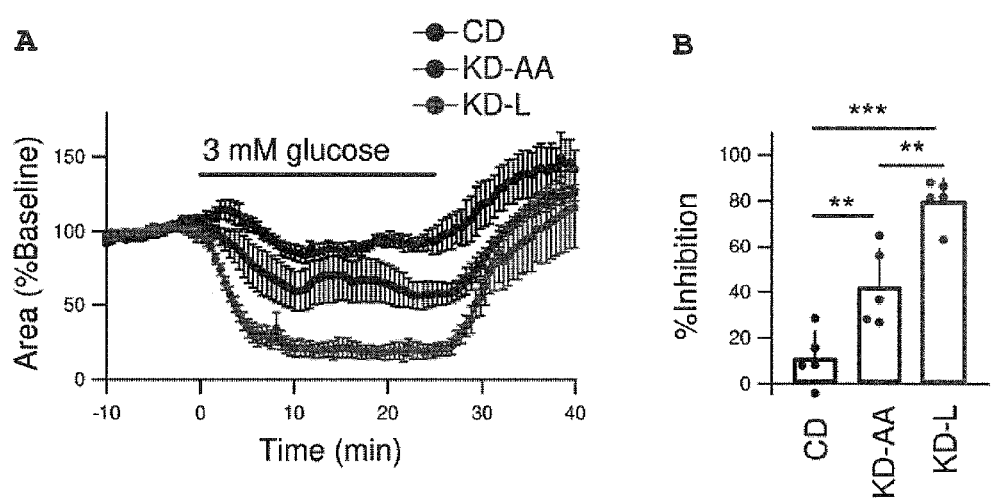
FIG. 2 shows representative data indicating that addition of a leucine-enriched amino acid mixture (e.g., Amino L40) enhanced the inhibitory effect of ketogenic diet in suppressing bicuculline-induced cell bursting. Data also indicate the effect is not mediated by the GABA(A) receptor. CD=control diet CRF-1, KD-AA=ketogenic diet supplemented with 3.3% casein composition amino acids; KD-L=ketogenic diet supplemented with 3.3% leucine-enriched amino acid mixture (e.g., Amino L40).

Three weeks after beginning the ketogenic diet, animals were sacrificed and appropriate tissues were collected. Extracellular recordings were obtained from hippocampal CA pyramidal cell layer in a cell burst assay. Briefly, electrical stimulation-induced seizure-like cell bursting was induced with 10 μM bicuculline (a GABA(A) antagonist). Glucose-sensitive cell bursting suppression was observed by changing glucose levels in the extracellular media from 11 mM to 3 mM for 25 minutes. Data indicate that supplementation with 3.3% leucine-enriched essential amino acid mixture enhanced the inhibitory effect of the ketogenic diet in suppressing bicuculline-induced cell bursting (FIG. 2). The KD-AA group significantly suppressed bursting compared to the control group, but the KD-L group showed a more potent suppressive action. This effect is not mediated by the GABA(A) receptor, indicating that the particular composition of amino acids in a mixture plays a role in suppression of seizure-like cell bursting; merely adding any mixture of amino acids to a ketogenic diet may not result in a protective effect.

Figure 3A:
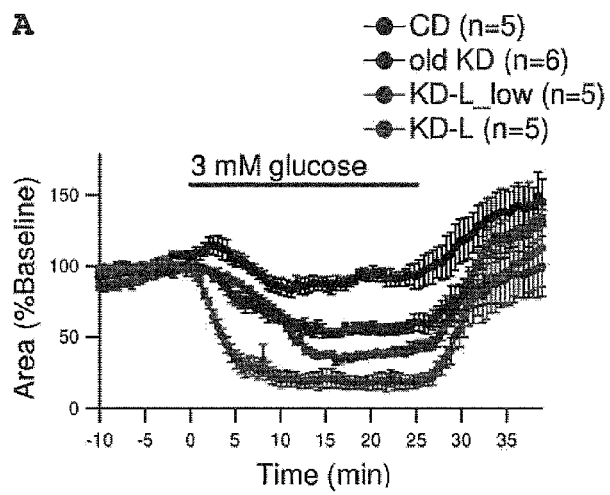
FIGS. 3A-3B show representative data indicating that leucine-enriched amino acid mixtures (e.g., Amino L40) enhanced the inhibitory effect of ketogenic diet in suppressing bicuculline-induced cell bursting in a dose-dependent manner. CD=control diet CRF-1; old KD=ketogenic diet (6:1 ketogenic ratio) without amino acid addition; KD-L=standard ketogenic diet supplemented with 3.3% leucine-enriched amino acid mixture (e.g., Amino L40); KD-L_low=standard ketogenic diet supplemented with 2.5% leucine-enriched amino acid mixture (e.g., Amino L40).
Figure 3B:
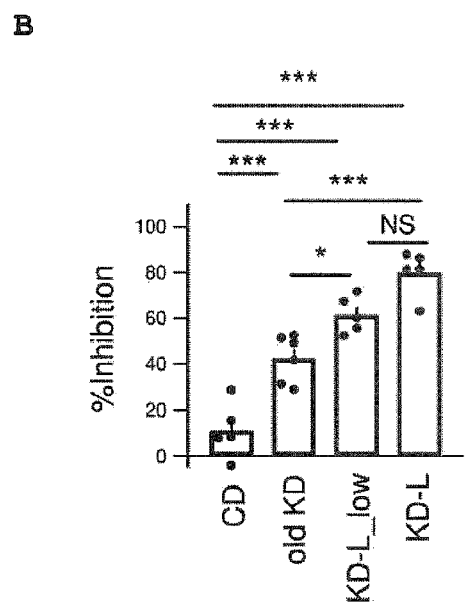

A dose response study was also performed using the cell burst assay described above. Two dosages of leucine-enriched amino acid mixtures were tested (KD supplemented with 3.3% leucine-enriched essential amino acid mixture, "KD-L"; KD supplemented with 2.5% leucine enriched amino acid mixture, "KD-L_low"). Data indicate a difference in response to the two doses of leucine-enriched amino acid mixtures (FIGS. 3A-3B). The shape of the 2.5% leucine-enriched amino acid dose mimics the KD alone but extends the response further (FIG. 3A). The 3.3% leucine-enriched amino acid dose has a curve of a different shape, indicating that cellular protection occurs more quickly, to a greater extent; the resolution path of the higher dose (e.g., 3.3%) also changes relative to the low (2.5% dose) and KD only-control (FIG. 3A). Data indicate that supplementation with 3.3% or 2.5% leucine-enriched essential amino acid mixtures significantly enhanced the inhibitory effect of the ketogenic diet (KD) in suppressing bicuculline-induced cell bursting relative to the KD alone (FIG. 3B).

In summary, data indicate supplementation of a ketogenic diet with leucine-enriched amino acid mixture improves suppression of cell-bursting relative to the casein-based mixture, and does so in a dose-dependent manner.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A ketogenic composition comprising: fat, a protein source, and carbohydrate, wherein: (a) the fat provides 60-90% of total calories of the composition and medium chain triglycerides (MCTs) provide between 10-40% of total calories of the composition; (b) the protein source comprises a non-casein protein and a leucine-enriched amino acid mixture; (c) and the ratio of calories fat to calories combined protein and net carbohydrate ranges from about 2:1 to about 4:1,
   wherein the leucine-enriched amino acid mixture comprises L-leucine, L-histidine, L-isoleucine, L-lysine, L-methionine, L-phenylalanine, L-threonine, L-tryptophan, and L-valine, and comprises leucine at a molar ratio between 30% and 70% with respect to total essential amino acids in the mixture.

2. The ketogenic composition of claim 1, wherein the protein source comprises a non-casein protein isolate, non-casein protein concentrate, non-casein protein hydrolysate, or a combination of the foregoing, optionally wherein the protein source is nutritionally complete.

3. The ketogenic composition of claim 1, wherein the leucine-enriched amino acid mixture comprises leucine at a molar ratio between 35% and 60% with respect to total essential amino acids in the mixture.

4. The ketogenic composition of claim 1, wherein each of the amino acids in the composition is present at the following molar composition ratio (%) with respect to total of essential amino acids in the composition: 0.1% to 5% of L-histidine, 5.0% to 15% of L-isoleucine, 30% to 70% of L-leucine, 8.0% to 25% of L-lysine, 2.0% to 10% of L-methionine, 2.5% to 8.0% of L-phenylalanine, 7.0% to 20% of L-threonine, 5.0% to 15% of L-valine, and 0.1% to 4.0% of L-tryptophan.

5. The ketogenic composition of claim 1, wherein the molar ratio of leucine to isoleucine ranges from about 1:1 to 4:1, the ratio of leucine to valine ranges from about 1:1 to about 4:1, or a combination of the foregoing.

6. The ketogenic composition of claim 1, wherein the fat comprises about 40% to about 50% MCTs by weight.

7. The ketogenic composition of claim 1 further comprising one or more vitamins and one or more minerals, optionally wherein the one or more vitamins comprise vitamin D, vitamin K1, and/or vitamin K2, and/or wherein the one or more minerals comprise calcium, magnesium and/or phosphorous.

8. The ketogenic composition of claim 1, wherein the composition is a solid, optionally wherein the solid is a powder.

9. The ketogenic composition of claim 1, wherein the composition is a liquid, optionally wherein the liquid is an aqueous liquid.

10. The ketogenic composition of claim 1, wherein the composition is nutritionally complete.

11. A method for dietary management of a disease or condition associated with clinical improvement after Ketogenic diet administration, the method comprising administering to the subject an effective amount of the composition of claim 1.

12. The method of claim 11, wherein the disease or condition is intractable epilepsy.

13. The method of claim 11, wherein the subject is following or has previously followed a ketogenic diet.

14. The method of claim 11, wherein the subject has been determined to be refractory to treatment with anti-epileptic drugs (AEDs).

15. The method of claim 11, wherein the subject is determined to have an improvement in clinical outcomes after administration of the ketogenic diet.

16. A method for treating intractable epilepsy in a subject comprising administering to the subject a leucine-enriched amino acid mixture comprising L-leucine, L-histidine, L-isoleucine, L-lysine, L-methionine, L-phenylalanine, L-threonine, L-tryptophan, and L-valine, wherein
   (i) the leucine is present at a molar ratio between 30% and 70% with respect to total essential amino acids in the mixture; and
   (ii) the molar ratio of leucine to isoleucine ranges from about 1:1 to 4:1 or the ratio of leucine to valine ranges from about 1:1 to about 4:1.

17. A method for reducing epileptic seizures in a subject comprising administering to the subject a leucine-enriched amino acid mixture comprising L-leucine, L-histidine, L-isoleucine, L-lysine, L-methionine, L-phenylalanine, L-threonine, L-tryptophan, and L-valine, wherein
   (i) the leucine is present at a molar ratio between 30% and 70% with respect to total essential amino acids in the mixture; and
   (ii) the molar ratio of leucine to isoleucine ranges from about 1:1 to 4:1 or the ratio of leucine to valine ranges from about 1:1 to about 4:1.

18. The method according to claim 16, wherein the intractable epilepsy is the epilepsy that is refractory to treatment with one or more anti-epileptic drugs (AEDs).

19. The method according to claim 16, wherein the subject has previously been administered a ketogenic formula or is currently following a ketogenic diet.

20. The method according to claim 16, wherein the subject is in a state of ketosis.

21. The method according to claim 16, wherein the leucine-enriched amino acid mixture accounts for between 1.0% and 6.0% of the subject's daily caloric intake.

22. A method for clinical dietary management of a disease or disorder of a subject on a ketogenic diet, comprising administering to the subject a leucine-enriched amino acid mixture comprising L-leucine, L-histidine, L-isoleucine, L-lysine, L-methionine, L-phenylalanine, L-threonine, L-tryptophan, and L-valine, wherein
(i) the leucine is present at a molar ratio between 30% and 70% with respect to total essential amino acids in the mixture; and
(ii) the molar ratio of leucine to isoleucine ranges from about 1:1 to 4:1 or the ratio of leucine to valine ranges from about 1:1 to about 4:1.

23. A method for inducing ketogenesis in a subject comprising administering to the subject a leucine-enriched amino acid mixture comprising L-leucine, L-histidine, L-isoleucine, L-lysine, L-methionine, L-phenylalanine, L-threonine, L-tryptophan, and L-valine, wherein
(i) the leucine is present at a molar ratio between 30% and 70% with respect to total essential amino acids in the mixture; and
(ii) the molar ratio of leucine to isoleucine ranges from about 1:1 to 4:1 or the ratio of leucine to valine ranges from about 1:1 to about 4:1.

24. The method according to claim 23, wherein the method further comprises administering a ketogenic diet to the subject.

25. A non-therapeutic method of inducing ketogenesis in a subject comprising administering to the subject a leucine-enriched amino acid mixture comprising L-leucine, L-histidine, L-isoleucine, L-lysine, L-methionine, L-phenylalanine, L-threonine, L-tryptophan, and L-valine, wherein
(i) the leucine is present at a molar ratio between 30% and 70% with respect to total essential amino acids in the mixture; and
(ii) the molar ratio of leucine to isoleucine ranges from about 1:1 to 4:1 or the ratio of leucine to valine ranges from about 1:1 to about 4:1.

26. The method according to claim 25, further comprising administering a ketogenic diet to the subject.

27. The method according to claim 25, wherein the non-therapeutic method is cosmetic or athletic performance-enhancing.

28. A method for treating disease or disorder in a subject selected from traumatic brain injury (TBI), neurodegenerative disease, cancer, obesity, diabetes, and diseases related to certain inborn errors of metabolism, comprising administering to the subject a mixture comprising L-leucine, L-histidine, L-isoleucine, L-lysine, L-methionine, L-phenylalanine, L-threonine, L-tryptophan, and L-valine, wherein
(i) the leucine is present at a molar ratio between 30% and 70% with respect to total essential amino acids in the mixture; and
(ii) the molar ratio of leucine to isoleucine ranges from about 1:1 to 4:1 or the ratio of leucine to valine ranges from about 1:1 to about 4:1.

29. The method according to claim 28, wherein the diseases related to inborn errors of metabolism are selected from glucose transporter syndrome and pyruvate dehydrogenase deficiency (PDH).

30. The method according to claim 28, wherein the cancer is selected from brain tumors.

* * * * *